United States Patent
Ke et al.

(10) Patent No.: US 7,259,850 B2
(45) Date of Patent: Aug. 21, 2007

(54) APPROACH TO IMPROVE ELLIPSOMETER MODELING ACCURACY FOR SOLVING MATERIAL OPTICAL CONSTANTS N & K

(75) Inventors: Chih-Ming Ke, Hsin-Chu (TW);
Pei-Hung Chen, Hsin Chu (TW);
Shinn-Sheng Yu, Taichung (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 441 days.

(21) Appl. No.: 10/757,204

(22) Filed: Jan. 14, 2004

(65) Prior Publication Data

US 2005/0151969 A1   Jul. 14, 2005

(51) Int. Cl.
*G01J 4/00* (2006.01)

(52) U.S. Cl. .................. 356/369; 356/630

(58) Field of Classification Search ........ 356/364–369, 356/630, 72–73; 250/559.28, 559.29, 256, 250/225
See application file for complete search history.

(56) References Cited

U.S. PATENT DOCUMENTS

| | | | |
|---|---|---|---|
| 4,826,321 A * | 5/1989 | Coates et al. ............ | 356/492 |
| 5,452,091 A * | 9/1995 | Johnson ................... | 356/445 |
| 5,798,837 A | 8/1998 | Aspnes et al. ........... | 356/369 |
| 6,057,928 A | 5/2000 | Li et al. .................. | 356/445 |
| 6,141,103 A * | 10/2000 | Pinaton et al. ........... | 356/369 |
| 6,151,116 A * | 11/2000 | Hirosawa ................. | 356/369 |
| 6,304,326 B1 | 10/2001 | Aspnes et al. ........... | 356/369 |
| 6,411,385 B2 | 6/2002 | Aspnes et al. ........... | 356/369 |
| 6,417,921 B2 | 7/2002 | Rosencwaig et al. ..... | 356/369 |
| 6,583,876 B2 * | 6/2003 | Opsal et al. ............. | 356/369 |
| 6,646,752 B2 * | 11/2003 | Chen et al. .............. | 356/630 |
| 6,671,047 B2 * | 12/2003 | Opsal et al. ............. | 356/369 |
| 6,710,889 B2 * | 3/2004 | Lee et al. ................ | 356/630 |

* cited by examiner

*Primary Examiner*—Sang H Nguyen

(57) ABSTRACT

A method of determining optical constants n and k for a film on a substrate is described. Optical measurements are preferably performed with an integrated optical measurement system comprising a reflectometer, spectral ellipsometer, and broadband spectrometer such as an Opti-Probe series tool from Therma-Wave. A beam profile reflectometer is employed to first determine the thickness of said film from a best fit of modeling data to experimental data. The thickness data is combined with the ellipsometer and spectrometer measurements to produce an experimental data output which is fitted with modeled information to determine a best fit of the data. Constants n and k are derived from the best fit of data. The method provides a higher accuracy for n and k values than by standard procedures which calculate n, k, and t simultaneously. The method may also be applied to bilayer or multi-layer film stacks.

19 Claims, 5 Drawing Sheets

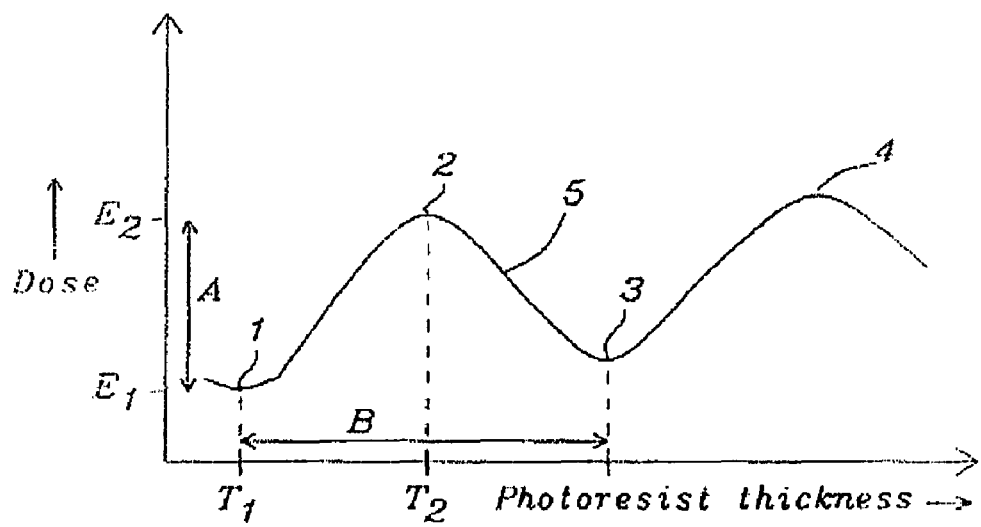
FIG. 1 - Prior Art
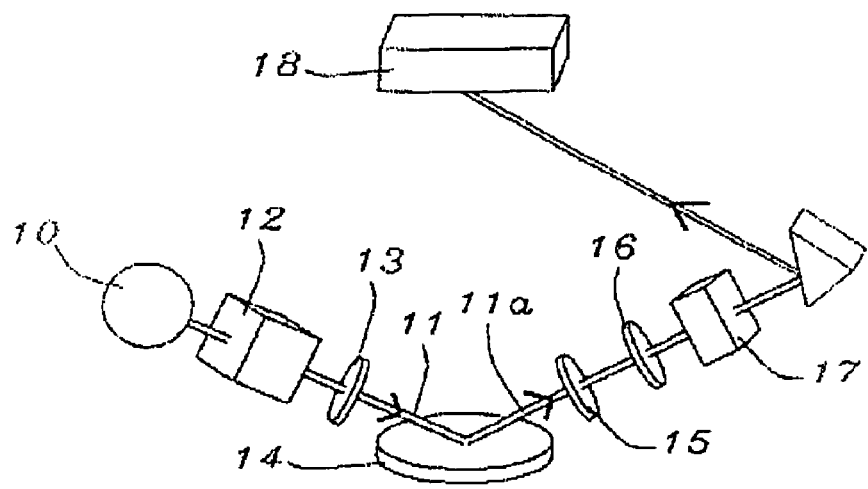
FIG. 2 - Prior Art

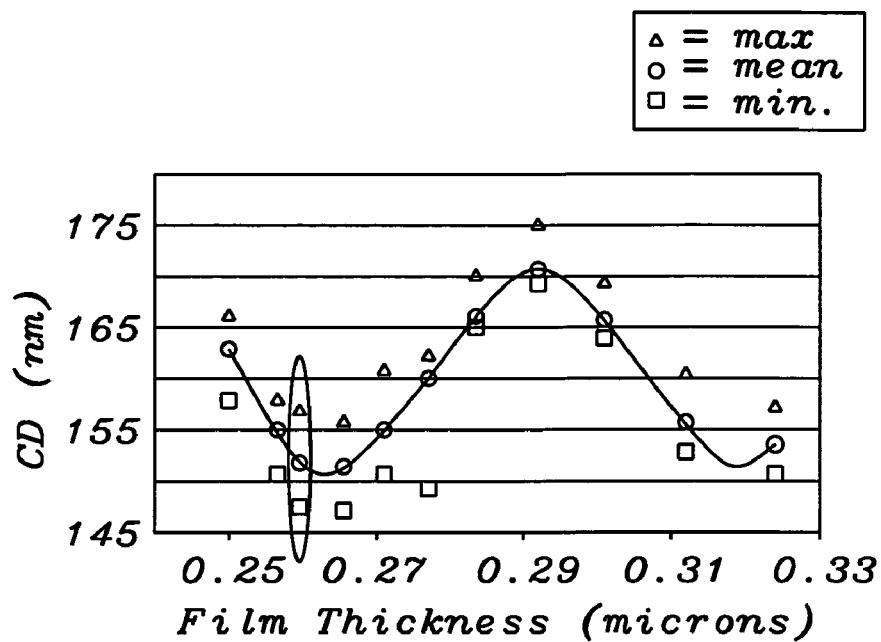
FIG. 3a - Prior Art
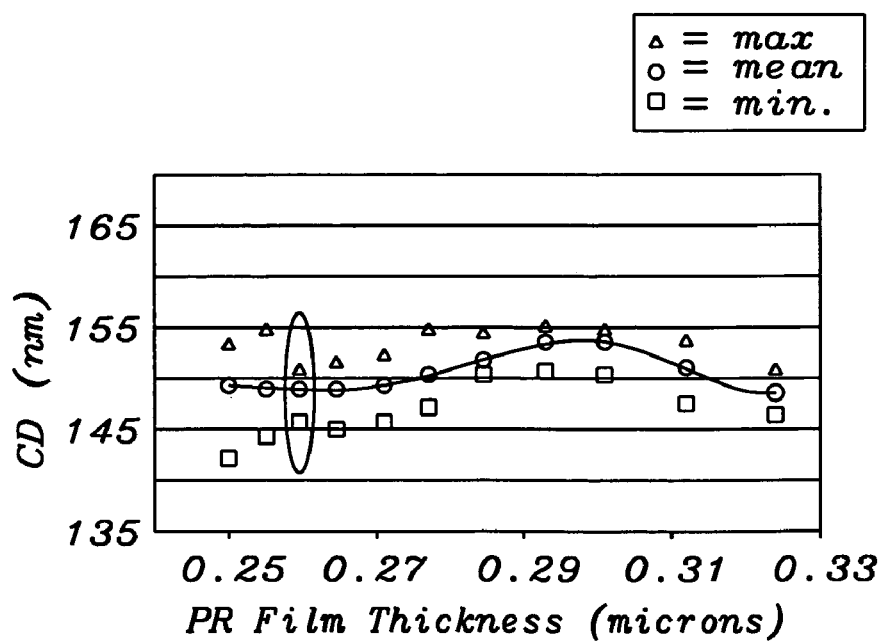
FIG. 3b - Prior Art

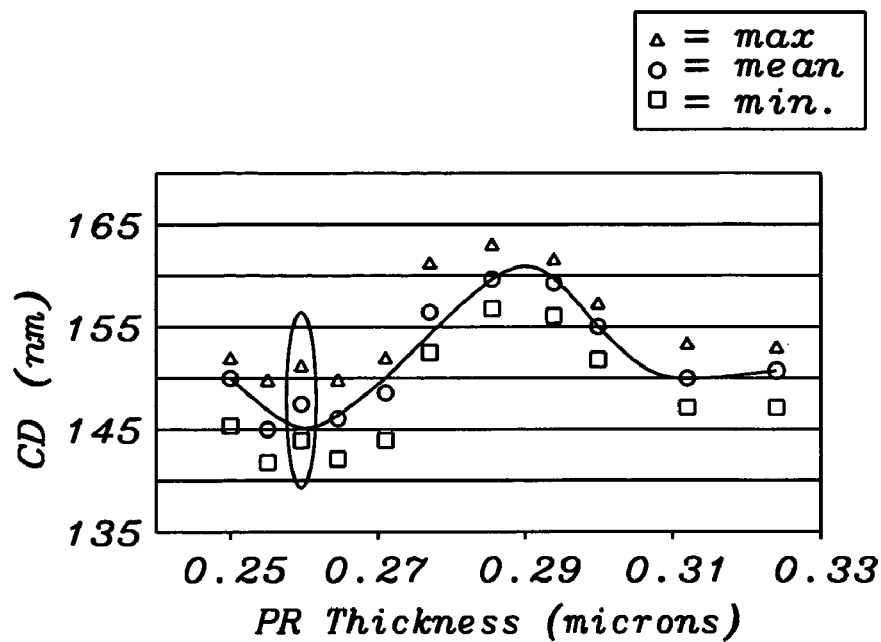
FIG. 3c – Prior Art
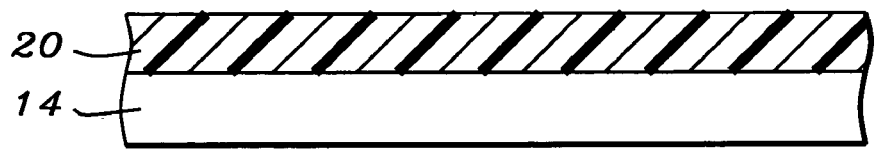
FIG. 4
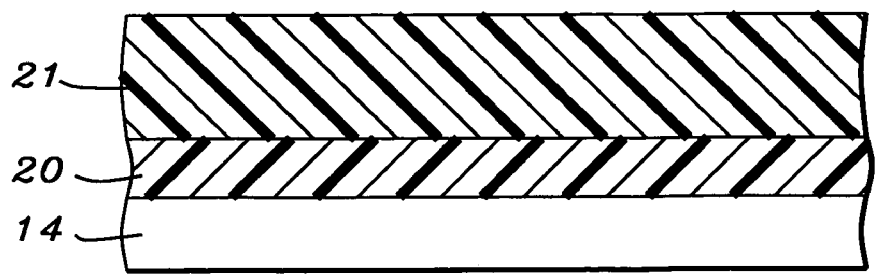
FIG. 5

APPROACH TO IMPROVE ELLIPSOMETER MODELING ACCURACY FOR SOLVING MATERIAL OPTICAL CONSTANTS N & K

FIELD OF THE INVENTION

The invention relates to the field of optical measurements, and more particularly, to a method of determining film thickness and refractive index (n and k) from optical measurements taken with an integrated system including an ellipsometer, reflectometer, and spectrometer.

BACKGROUND OF THE INVENTION

Photolithography is a key component of semiconductor device manufacturing. A photosensitive composition that is often called a photoresist or resist is spin coated on a substrate and is patterned with a mask and an exposure system. The pattern is subsequently transferred into one or more underlying layers by a plasma etch method. Process control of the lithography step is crucial in order to maintain the critical dimension (CD) of features in the printed pattern within a specified range.

Characterizing the optical properties and thickness of the photoresist and underlying layers is necessary to establish CD control. Typically, one or more wavelengths in a range from about 10 nm to about 500 nm is used to expose the photoresist. The light that passes through the photoresist may reflect off underlying layers and pass through the photoresist a second time and can either constructively or destructively interfere with radiation that passes in the opposite direction. Depending on the thickness of the resist, the total energy or accumulated radiation per unit area (referred to as milliJoules/cm$^2$) required to print a feature at a desired CD varies according to the curve shown in FIG. 1 where the plot of thickness vs. exposure dose forms a sinusoidal curve 5 that has minima 1, 3 and maxima 2, 4. This "swing" curve has an amplitude A between a minimum and a maximum energy and a periodicity B defined as the distance (thickness) between two adjacent minimum points or between two adjacent maximum points on the curve 5. The magnitude of periodicity B is related to the wavelength of the exposing radiation. The amplitude A is calculated by dividing the difference between the energy for maximum point 2 ($E_2$) and the energy for minimum point 1 ($E_1$) by the average of $E_1$ and $E_2$ which is $(E_2-E_1)/(E_1+E_2/2)$ and this value can be as large as 0.3 which is a swing of 30% in dose. Clearly, an accurate thickness measurement is needed in order to determine that a resist thickness target and thickness uniformity on a wafer is within a tight specification so that a large swing effect can be avoided.

The swing amplitude has a detrimental effect on the lithography process, especially if the magnitude is more than a few % of the average dose. Consider the condition in FIG. 1 where a swing amplitude of 30% is realized as determined previously for $E_1$ and $E_2$ and the patterned feature is a contact hole. If a dose $E_1$ is used to form a contact hole in a photoresist with a thickness $T_1$ on one wafer and the same mask and dose $E_1$ are used to pattern the same photoresist but with a thickness $T_2$ on a second wafer, then the size of the hole with thickness $T_1$ will be much larger than the hole size with thickness $T_2$ since the latter requires a much higher energy to form a hole to a predetermined size. The size difference in space width of the hole is likely to be much greater than the ±10% maximum variation typically allowed for a manufacturing process. Therefore, it is important to keep film thickness uniform within a wafer and from wafer to wafer and to minimize the swing curve to avoid a wide range of CD sizes.

In some situations, an anti-reflective coating (ARC) is applied to the substrate prior to the photoresist coating in order to control reflectivity during the photoresist exposure step and enable a larger process latitude by reducing the swing effect. The ARC which may be an organic or inorganic material is normally much thinner than the photoresist layer and is most effective on relatively flat substrates. However, thickness control for the ARC layer is also important. FIGS. 3a-3c demonstrate how the magnitude of a photoresist swing curve changes as a silicon nitride ARC thickness is varied. The silicon nitride layer has a thickness of 540 Angstroms in FIG. 3a, 750 Angstroms in FIG. 3b, and 1030 Angstroms in FIG. 3c. Reflectivity is minimized by keeping the film thickness of both photoresist and the underlying ARC layer within a tight specification and by tuning the optical constants (n and k) of both layers, if possible. Therefore, it is important to use a method for measuring optical constants n and k that is accurate and reliable and one that requires a minimum of time since several iterations in the photoresist and ARC development process may be necessary before a manufacturable photoresist or ARC product is achieved. In other words, optical film measurements are as important to optimizing a new photoresist or ARC formulation as to controlling a patterning process in manufacturing.

Spectroscopic ellipsometry (SE) is a well accepted tool to extract optical constants n and k in the industry and may be combined with other optical measurement instruments such as a spectrometer and reflectometer. For example, U.S. Pat. Nos. 5,798,837, 6,304,326, 6,411,385, and 6,417,921 assigned to Therma-Wave describe a composite optical measurement system that involves internal calibration as well as n and k measurements of single layer or multi-layer film stacks. Therma-Wave is the only SE tool company that offers an integrated system (Opti-Probe series) with the "expert" level or independent optical thickness measurement components called BPR (Beam Profile Reflectometry) and BPE (Beam Profile Ellipsometry).

A simplified version of a spectroscopic ellipsometry apparatus is shown in FIG. 2. Deep UV and visible sources 10 provide a beam 11 that is polarized by polarizer 12 and focused by a lens 13 onto a wafer or substrate 14 upon which a sample film has been deposited. The wavelength and incident angle of the beam can be varied. The reflected beam 11a passes through a collimating lens 15, a compensator 16 which rotates in this case, an analyzer 17, and into a detector 18. Ellipsometry does not directly measure film thickness or optical constants n (index of refraction) and k (extinction coefficient) but provides up to three parameters, cos Δ, sin Δ, and tan ψ, which are converted to the complex Fresnel reflection coefficients $r_P$ and $r_S$. Here the "p" refers to light polarization parallel to the plane of incidence and "s" refers to light polarization perpendicular to the plane of incidence. SE measures the complex ratio $r_P/r_S$ as a function of wavelength. Coefficients $r_P$ and $r_S$ contain information on how the magnitude and polarization of the incident light beam are changed by the film on substrate 14 according to the equations: $E_P$,ref=$r_P$×$E_P$,inc and $E_S$,ref=$r_S$×$E_S$,inc where E is the electric field magnitude and "inc" and "ref" refer to incident and reflected light, respectively.

FIG. 6 is a flow chart depicting how the data from integrated optical measurement tools in an Opti-Probe system comprising a broadbeam spectrometer (BB), a spectroscopic ellipsometer (SE) and a beam profile reflectometer (BPR) is used to calculate thickness (t) and n and k values. The BPR component includes a laser that directs a 675 nm beam onto the sample which is then reflected to a BPR analyzer. It should be noted that the three components (BB, SE, BPR) are connected to the same processor so that the data output from each of the three components can be analyzed simultaneously. In step 30, the substrate with the sample film is positioned on a stage within the integrated system. The sample is probed at various wavelengths in step 31 and the data from the three components is weighted in step 32 according to a percentage that may be X % BPR, Y % SE, and Z % BB where X=55, Y=18, and Z=27, for example. An experimental data output is provided in step 33 and collected in the processor.

In step 34, film stack information such as assumed film thickness and approximate n and k values of the film are entered into a modeling program in the processor. The model is exercised (step 35) in the processor to generate a simulated set of data that can be compared to the experimental data obtained in step 33. The fitting of experimental data to modeling data in step 36 may involve several iterations of changing the modeled input until a best fit of modeling data to experimental data is obtained in step 37. Once a best fit is achieved, the program provides values for n, k, and thickness simultaneously. Unfortunately, the accuracy of the n and k values are strongly dependent on the application engineer's experience. A wrong initial guess for the regression fitting in the modeling phase will turn out erroneous n and k values and unreliable mapping signatures. In order to reduce the potential error introduced by modeling a wrong initial setting or by a low instrument signal to noise ratio, a more robust methodology for solving optical constants n and k is required.

One additional application of the index of refraction as described in U.S. Pat. No. 6,057,928 is that it can be used to determine a dielectric constant. The index of refraction is measured by impinging a high frequency beam on a sample and monitoring the phase change and field reflectance for a variety of incident angles.

SUMMARY OF THE INVENTION

An objective of the present invention is to provide a more reliable method of determining optical constants n and k that has higher accuracy.

A further objective of the present invention is to make use of existing tools for determining n, k, and thickness of films on substrates.

A still further objective is to provide a method for determining n and k that enables improved process control for patterning photoresists.

In one embodiment, these objectives are accomplished by providing a substrate having a sample film such as an anti-reflective coating or a photoresist layer to be characterized. The substrate is positioned on a stage in an integrated optical measurement system comprising a spectral ellipsometer, a broadband spectrometer, and a reflectometer. Preferably, the measurement is performed on an Opti-Probe instrument from Therma-Wave which is currently the only company with an integrated system. Initially, a beam profile reflectometer measurement is performed and the data output is fit to a model to extract a thickness for the sample from the best fit of the data. The thickness data is then combined with the ellipsometer and spectrometer measurements to generate an experimental data output. The experimental data is fitted with modeled data and a best fit of the data is found. The best fit of the data provides n and k for the sample film with a higher accuracy than prior art.

Alternatively, the present invention may be used to determine n, k, and thickness (t) for a top layer in a bilayer or trilayer film stack on a substrate. In one embodiment, the n, k, and t values for the underlayer in a bilayer stack are inputted along with a beam profile reflectometer measurement to determine the thickness for the top layer which is typically a photoresist. The top layer thickness data is then combined with ellipsometer and spectrometer measurements to generate an experimental data output which is fitted with modeled data to arrive at an n and k for the top layer. The trilayer stack may comprise a top photoresist layer, a middle organic ARC layer, and a bottom inorganic layer. In this embodiment, n, k, and t values for the inorganic layer may be determined before the ARC layer is coated. Then the n, k, and t values for the ARC may be determined as described for a bilayer stack above. Finally, the n, k, and t results for the top layer are generated.

BRIEF DESCRIPTION OF THE DRAWINGS

FIG. 1 is a drawing illustrating a swing curve in which the energy required to pattern a photoresist layer varies with the photoresist thickness.

FIG. 2 is a view showing the various elements of a spectral ellipsometer.

FIGS. 3a-3c are swing curves that illustrate how a CD varies while exposing a photoresist at a fixed dose on three different silicon nitride ARC thicknesses.

FIG. 4 is a cross-sectional view of a photoresist layer on a substrate.

FIG. 5 is a cross-sectional view showing two layers deposited on a substrate.

DETAILED DESCRIPTION OF THE INVENTION

Preferred embodiments of the present invention will be described with reference to the drawings in FIGS. 4, 5 and 7. In one embodiment, the invention is a method of characterizing n and k values in a single layer photoresist with greater accuracy than in prior art. Improved accuracy results in characterization that leads to better understanding of properties that affect n and k in the material development process and reduces the cycle time for introducing new materials into a manufacturing environment. Alternatively, the method may be used as a means of process control in a manufacturing line. For example, anti-reflective films that are deposited by a chemical vapor deposition process may have n and k values that vary somewhat from lot to lot because of a slight shift in process conditions. The method could be used to monitor selected films to ensure that there is no drift in n and k that might cause a reduction in process control and a lower yield of product.

Referring to FIG. 4, a substrate 14 is provided that is typically silicon but may be based on silicon-on-insulator, silicon-germanium, or other semiconductor substrates used in the art. For example, the substrate 14 could be a circular wafer that is pictured in FIG. 2. An organic or inorganic layer 20 is deposited on the substrate 14 to form a film with an intended thickness in the range of about 300 to 10000 Angstroms. The layer 20 may be a commercially supplied material or an experimental formulation that is being optimized in a development mode. The layer 20 may comprise a photoresist, an anti-reflective layer (ARC), or an underlayer for a bilayer film stack as appreciated by those skilled in the art. While photoresists and underlayers are normally applied in a spin-on process, an ARC may be formed by a spin-on step or by a CVD method.

Figure 7:
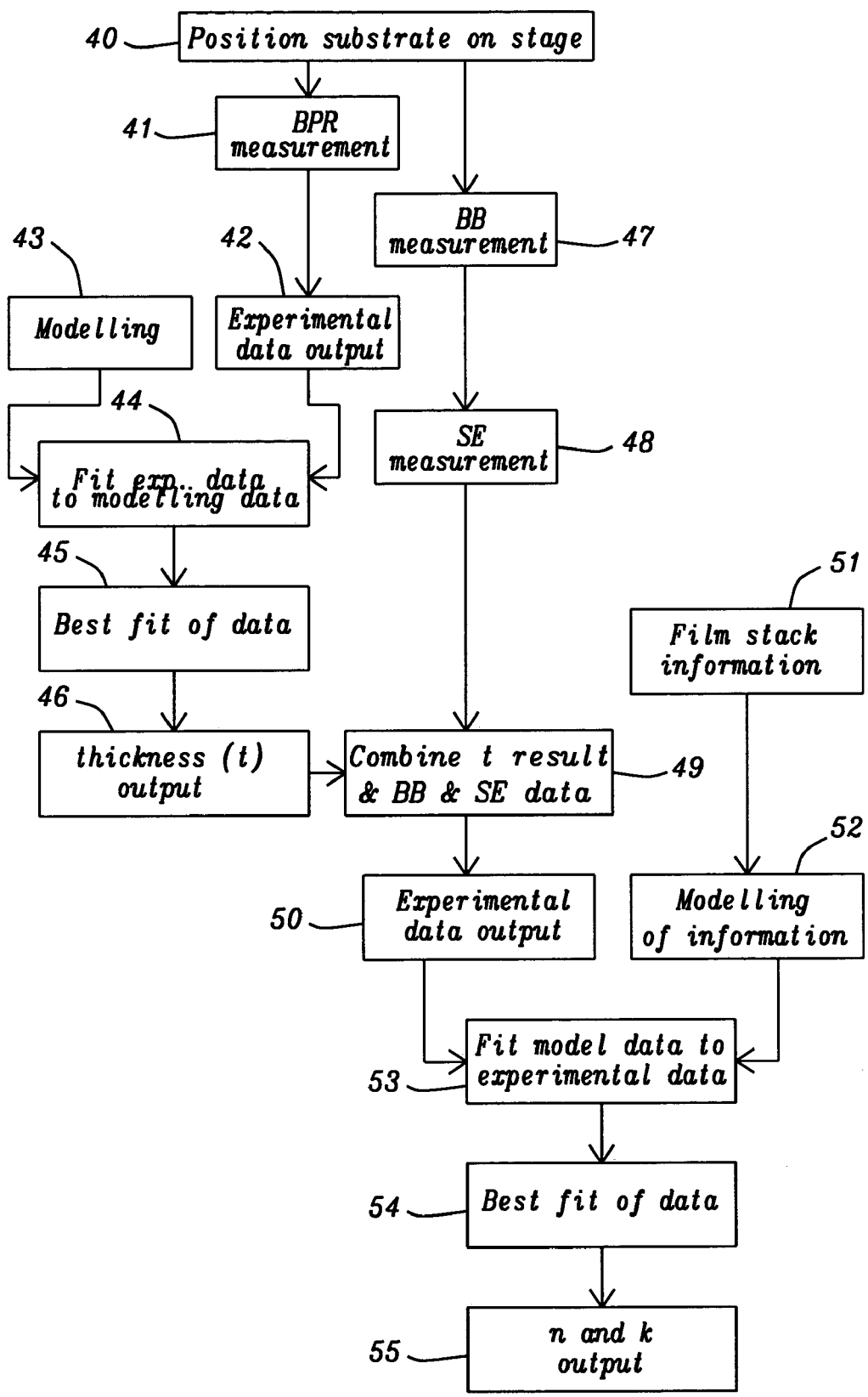
FIG. 7 is a flow diagram showing how n, k, and t are determined according to an embodiment of the present invention.

Referring to step 40 in FIG. 7, the substrate 14 having an organic or inorganic layer 20 is positioned in a chamber in an integrated optical measurement system comprised of a beam profile reflectometer (BPR), a spectral ellipsometer (SE), and a broadband spectrometer (BB). Preferably, the integrated system is an Opti-Probe instrument from Therma-Wave or one with equivalent capability. A BPR measurement is taken in step 41 using a polarized 675 nm light beam from a diode laser that is focused to a 0.9 micron spot size on the substrate 14. The intensity of reflected light depends on the parameters n, k, and t of the layer 20 on substrate 14 and on the angle of incidence of the impinging beam on substrate 14. Two detector arrays, one for reflected light in a plane parallel to the polarization direction and one for reflected light in a plane perpendicular to the polarization direction collect the reflected light. The BPR is considered to be an independent optical thickness measurement component of the integrated system.

In step 42, experimental data output is produced in the form of reflectivity signals that are referred to as A and B profiles. The profiles which are the reflectivity from layer 20 are normalized to the reflectivity of silicon. Modeled profiles are obtained in step 43 which involves inputting information such as equations that predict reflectivity at the interface between air and layer 20 and at the interface of layer 20 on substrate 14 as is understood by those skilled in the art.

Step 44 involves fitting the experimental A and B profiles to the modeled profiles in a processor to determine a best fit of the data (step 45). There may be several iterations of modifying the inputted information to generate modeled profiles before a good overlap with experimental profiles is found and a best fit is achieved. The best fit (step 45) is determined for one value of the unknown parameters which is layer 20 thickness. The thickness (t) output data 46 is stored in the processor and will be used for a subsequent modeling step to be described later.

Figure 6:
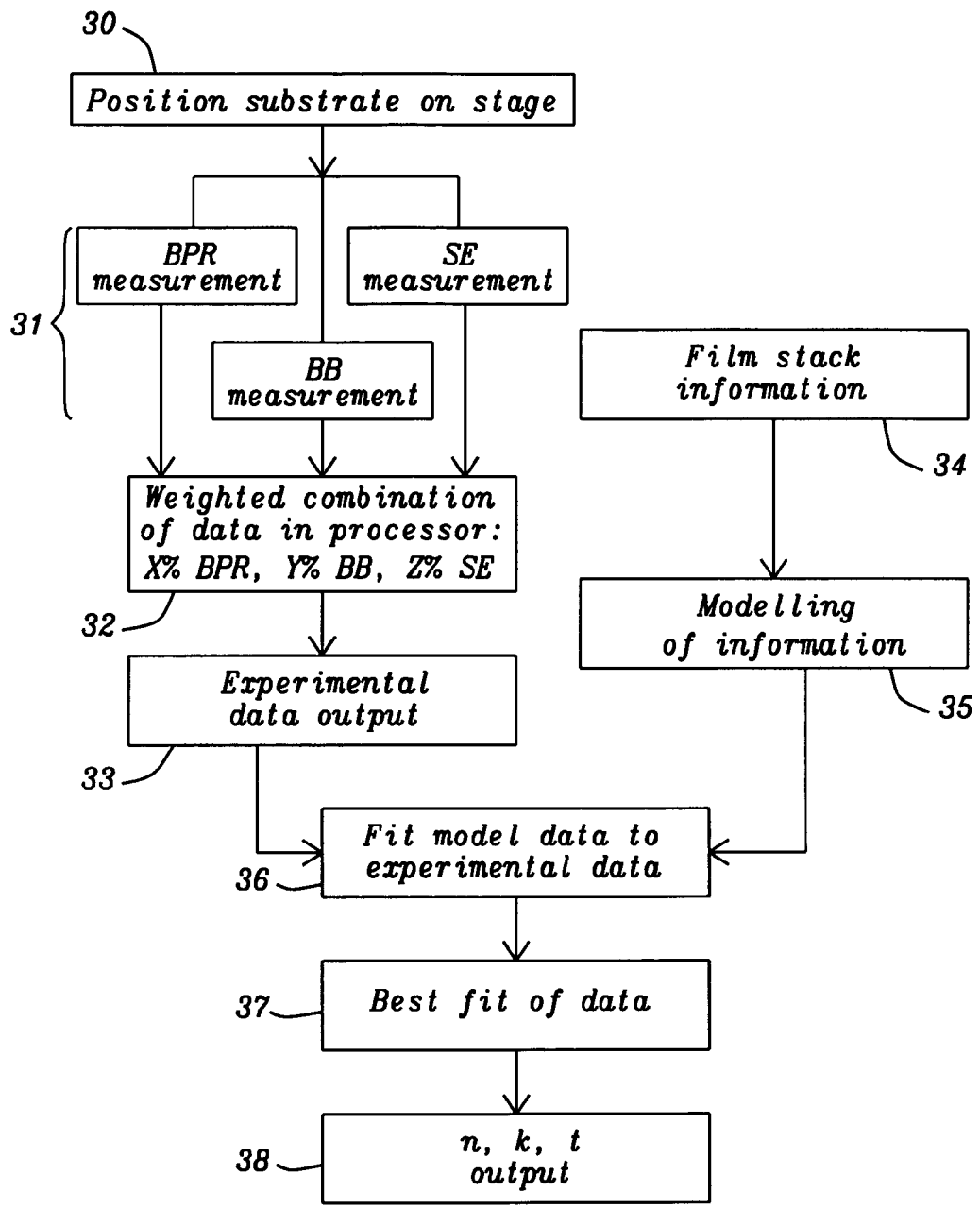
FIG. 6 is a flow diagram that shows how optical measurements are used to determine n, k, and thickness t by a prior art process.

Table 1 indicates that an improvement in accuracy is achieved by determining thickness (t) in this manner compared to the prior art method of calculating n, k, and t simultaneously. In this example, layer 20 is a commercially available organic ARC. Using the traditional method as shown in FIG. 6, a thickness of 315.88 Angstroms is determined with a range of values of 15.97 Angstroms. By following a method described for the first embodiment, a thickness of 306.45 Angstroms and a range of 7.62 Angstroms is calculated. Since a smaller range corresponds to a higher degree of certainty in the measurement, a higher accuracy is realized with the present invention.

TABLE 1

Organic ARC thickness, n and k at 248 nm

| Method | Thickness (Angstroms) | range | (n) | range | k | range |
|---|---|---|---|---|---|---|
| Traditional (n, k, t) all at once | 315.88 | 15.97 | 1.8364 | 0.1835 | 0.6248 | 0.1481 |
| Thickness first, then n & k | 306.45 | 7.62 | 1.8078 | 0.0221 | 0.6558 | 0.0345 |

Optionally, the integrated optical measurement system may include a Beam Profile Ellipsometry (BPE) component that is used to independently determine the thickness of the organic or inorganic layer 20.

Next, a BB measurement 47 and a SE measurement 48 are taken by directing wavelengths in the 190 to 800 nm range on the same layer 20 on substrate 14 but preferably in a different location than the spot where the BPR measurement was performed. The BB and SE measurements provide up to three parameters, cos $\Delta$, sin $\Delta$, and tan $\psi$, which are converted to reflection coefficients $r_P$ and $r_S$. The output data from the BB and SE measurements is combined in step 49 with the thickness output data 46 to give an experimental data output 50 for n and k. This calculation is performed in a processor supplied by Therma Wave but with a new algorithm created by the user as is understood by those skilled in the art.

Information on the layer 20 properties including the thickness output data 46 is then inputted into the processor in step 51. The information is modeled in step 52 with a Critical Point method otherwise known as a "harmonic oscillator approximation" to produce predicted values for parameters, cos $\Delta$, sin $\Delta$, and tan $\psi$. Since the thickness has already been determined, there is one less floating parameter to manipulate in building a correct dispersion model.

The modeled data from step 52 is fit to the experimental data output 50 in the processor in step 53. There may be several iterations of modifying the modeling data before a good overlap with the experimental data output is obtained. When a best fit of the data is achieved in step 54, n and k values for layer 20 are provided as output 55.

Table 1 indicates that an improvement in accuracy is achieved by determining n and k in this manner compared to the prior art method of calculating n, k, and t simultaneously. For example, using the traditional method of measuring the commercially available ARC layer, n is 1.8364 at a wavelength of 248 nm with a range of 0.1835 while k is 0.6248 with a range of 0.1481. Following the method of the first embodiment, n is 1.8078 with a range of 0.0221 and k is 0.6558 with a range of 0.0345. Since a smaller range corresponds to a higher degree of certainty in the measurement, a higher accuracy is realized with this invention. Furthermore, there is less opportunity for operator error during the modeling process since one of the floating parameters in a prior art method, namely thickness, is fixed in this case by determining thickness before calculating n and k values.

By inputting more accurate n and k data for an ARC, more reliable reflectivity curves such as those in FIGS. 3a-3c are generated. In other words, the ARC thickness that provides the smallest swing curve and highest degree of process latitude is more highly pinpointed by employing n and k values generated by the present invention.

In another example, n and k are determined for a commercially available 193 nm organic ARC that was coated at different thicknesses and the results from a prior art method (CP) are compared to values obtained by following the procedure described for the first embodiment which is listed as T+CP. The CP method involves calculating n, k and t simultaneously while the (T+CP) method determines the thickness value first and then uses the thickness result to generate a solution for n and k.

TABLE 2

Organic ARC thickness, n and k at 193 nm

| Slot # | Thickness (Ang.) | Model | n | 1 sigma (n) | (k) | 1 sigma (k) |
|---|---|---|---|---|---|---|
| Slot 3 | 300 | CP | 1.739 | 0.002 | 0.621 | 0.002 |
| Slot 3 | 300 | T + CP | 1.724 | 0.001 | 0.62 | 0.003 |
| Slot 2 | 600 | CP | 1.741 | 0.002 | 0.622 | 0.002 |
| Slot 2 | 600 | T + CP | 1.737 | 0.002 | 0.628 | 0.001 |
| Slot 4 | 600 | CP | 1.741 | 0.002 | 0.621 | 0.002 |
| Slot 4 | 600 | T + CP | 1.738 | 0.001 | 0.628 | 0.001 |
| Slot 1 | 900 | CP | 1.731 | 0.002 | 0.618 | 0.002 |
| Slot 1 | 900 | T + CP | 1.726 | 0.001 | 0.617 | 0.001 |

Slots 1 to 4 represent substrates having various ARC film thicknesses ranging from 300 to 900 Angstroms. Results for n and k and corresponding 1 sigma values are shown for each thickness. In most cases, the certainty or accuracy of the n and k results are improved by implementing the T+CP model as demonstrated by lower 1 sigma values for the method of the first embodiment.

In a second embodiment, the invention is a method of characterizing n and k values of films in a multi-layer stack with greater accuracy than in prior art. Although several layers can be applied to construct a stack on a substrate, a description for measuring a two layer stack will be provided in this embodiment.

Referring to FIG. 5, a substrate 14 is provided as described in the first embodiment that is typically a silicon wafer. An organic or inorganic layer 20 hereafter referred to as underlayer 20 is deposited on the substrate 14 with an intended thickness in the range of about 300 to 10000 Angstroms. The underlayer 20 may be a commercially supplied material or an experimental formulation that is being optimized in a development mode. Moreover, the underlayer 20 may comprise an anti-reflective layer (ARC) or a photoresist that has been hard baked to a temperature of about 200° C. to 250° C. While a photoresist is normally applied in a spin-on process, an ARC may be formed by a spin-on step or by a CVD method. The underlayer 20 may also be the bottom layer of a bilayer stack in which the lower layer is selected for its anti-reflective and planarization properties. It is desirable to have an underlayer 20 in a bilayer stack which has n and k values that minimize the amount of reflected radiation during a patterning step of an overlying photoresist.

In the exemplary embodiment, the underlayer 20 is the ARC coating whose optical constants n and k were determined in the first embodiment and provided in Table 1. In general, the n and k values for underlayer 20 in the second (bilayer) embodiment should be determined according to the first embodiment before the second layer 21 is coated.

A photoresist layer 21 is formed on the underlayer 20 by spin coating a photosensitive composition available from a commercial supplier and baking to form a film. Optionally, the photoresist layer 21 is formed from a photosensitive composition that is in a development mode. The photoresist layer 21 is usually baked in a temperature range of about 90° C. to 150° C. which removes residual organic solvent without degrading the various components of the film. Since the underlayer 20 was baked at a higher temperature, there is no mixing of the underlayer 20 and photoresist layer 21. In a bilayer stack, the photoresist layer 21 may be a silicon containing photoresist that is selected for its etch resistance property. The more common wavelengths used for patterning a photoresist layer 21 are 365 nm (i-line), 248 nm (Deep UV), and 193 nm (ArF) although one or more wavelengths between about 10 nm and 500 nm may be employed for patternwise exposing a photoresist layer. The target thickness of the photoresist layer 21 is normally is about 1000 to 10000 Angstroms.

Referring to step 40 in FIG. 7, the substrate 14 having an underlayer 20 and the photoresist layer 21 is positioned in a chamber in an integrated optical measurement system comprised of a beam profile reflectometer (BPR), a spectral ellipsometer (SE), and a broadband spectrometer (BB). Preferably, the integrated system is an Opti-Probe instrument from Therma-Wave or one with equivalent capability. A BPR measurement is taken in step 41 using a polarized 675 nm light beam from a diode laser that is focused to a 0.9 micron spot size on the substrate 14. The intensity of reflected light depends on the parameters n, k, and t of the underlayer 20 and photoresist layer 21 on substrate 14 and on the angle of incidence of the impinging beam on substrate 14. Two detector arrays, one for reflected light in a plane parallel to the polarization direction and one for reflected light in a plane perpendicular to the polarization direction collect the reflected light.

In step 42, experimental data output is produced in the form of reflectivity signals that are referred to as A and B profiles. The profiles which are the reflectivity from the bilayer stack containing underlayer 20 and photoresist layer 21 are normalized to the reflectivity of silicon. Modeled profiles are obtained in step 43 which involves inputting information such as equations that predict reflectivity at the interface of air and photoresist layer 21 and at the interface of underlayer 20 and photoresist layer 21, and the n, k, and t values of underlayer 20 that were determined in a previous experiment by a method of the first embodiment. The n, k, and t values for underlayer 20 are inputted into a program that is used to calculate n and k for the photoresist layer 21.

Step 44 involves fitting the experimental A and B profiles to the modeled profiles in a processor to determine a best fit of the data (step 45). There may be several iterations of modifying the inputted information to generate modeled profiles in step 43 before a good overlap with experimental profiles is found and a best fit is achieved. The best fit (step 45) is determined for one value of the unknown parameters which is photoresist layer 21 thickness. The thickness output data 46 for photoresist layer 21 is stored in the processor and will be used for a subsequent modeling step to be described later. It is understood that thickness output data 46 for underlayer 20 is already stored in the processor from a previous measurement. Optionally, the integrated optical measurement system may include a BPE component that is used to independently determine the thickness of the photoresist layer 21, Next, a BB measurement 47 and a SE measurement 48 are taken by directing wavelengths in the 190 to 800 nm range onto the same photoresist layer 21 on substrate 14 but preferably in a different location than at the spot where the BPR measurement was performed. The BB and SE measurements provide up to three parameters, cos Δ, sin Δ, and tan ψ, which are converted to reflection coefficients $r_P$ and $r_S$. The output data from the BB and SE measurements are combined in step 49 with the thickness output data 46 for underlayer 20 and photoresist layer 21 and with n and k values for underlayer 21 determined in a previous measurement to provide an experimental data output 50 for photoresist layer 21. These calculations are performed by a program in the Therma Wave processor. As mentioned previously, the user may create a new algorithm to be employed for the calculations rather than use one supplied with the Opti-Probe measurement system.

Information including the thickness output data 46 for photoresist layer 21, and n, k, and t values for underlayer 20 obtained in earlier measurements are then inputted into the processor in step 51. The information is modeled in step 52 with a Critical Point method to produce predicted values for parameters, cos Δ, sin Δ, and tan ψ. Since the thickness for the photoresist layer 21 has already been determined, there is one less floating parameter that has to be manipulated to build a correct dispersion model which reduces the chance for error in the modeling step.

The modeled data from step 52 is fit to the experimental data output 50 in the processor in step 53. There may be several iterations of modifying the modeling data before a good overlap with the experimental data output is obtained. When a best fit of the data is achieved in step 54, n and k values for the photoresist layer 21 are provided as output 55.

Although the data shown in Table 1 is for underlayer 20 obtained in the first embodiment, a similar set of data is collected for photoresist layer 21 that indicates an improvement in accuracy is achieved by determining n and k in this manner compared to the prior art method of calculating n, k, and t simultaneously. A smaller range of values collected during the calculations corresponds to a higher degree of certainty in the measurements and a higher accuracy is realized with this invention. Furthermore, there is less opportunity for operator error during the modeling process since one of the floating parameters in a prior art method, namely thickness, is fixed in this case by determining thickness before calculating n and k values.

By inputting more accurate n and k data for an underlayer 20 and photoresist layer 21, more reliable reflectivity curves such as those shown in FIGS. 3a-3c are generated. In addition, a better match is able to be made between n and k values for underlayer 20 with n and k values for photoresist layer 21 to reduce reflectivity between the two layers and minimize the swing curve. Those skilled in the art will appreciate that n and k for an underlayer, particularly an inorganic ARC that is deposited by a CVD method, may be readily tuned to match n and k values for a commercially available photoresist. Therefore, improved n and k accuracy leads to a larger process window during a photoresist patterning step. As a result of a higher degree of certainty in the n and k values for the underlayer 20 and photoresist layer 21, a higher yield of product is achieved and less rework is necessary because film thicknesses in a bilayer stack are more accurate and are maintained within specified limits with a higher degree of control.

The second embodiment also encompasses a trilayer system. For example, an inorganic layer such as silicon nitride or silicon oxynitride may be deposited on a substrate followed by coating an organic ARC film and then a photoresist layer. In this case, the n, k, and t values for the inorganic and ARC layers could be found by forming a single layer film for each on two different substrates and following the method described in the first embodiment to determine n, k, and t separately for the inorganic film and ARC film. Optionally, the n, k, and t values for the inorganic layer could be generated before forming the ARC layer on the inorganic layer. The ARC layer could then be formed on the inorganic layer and treated as the top layer in a bilayer stack to generate n, k, and t as described in the second embodiment. After coating the photoresist layer on the ARC layer, the thickness of the photoresist layer is determined in steps 40-46 similar to the photoresist layer 21 on underlayer 20 in a bilayer stack.

In steps 49-54, the photoresist thickness as well as the n, k, and t values for the inorganic layer and ARC layer and BB 47 and SE 48 measurements of the photoresist layer in the trilayer stack are used to determine n and k for the photoresist layer. As a result of a higher degree of certainty in the n and k values for the inorganic layer, ARC layer, and top photoresist layer, a higher yield of product is achieved and less rework is necessary because film thicknesses in the trilayer stack are more accurate and are thereby maintained within specified limits with a higher degree of control.

While this invention has been particularly shown and described with reference to, the preferred embodiments thereof, it will be understood by those skilled in the art that various changes in form and details may be made without departing from the spirit and scope of this invention.

We claim:

1. A method for obtaining values for optical constants n and k for a layer on a substrate comprising:
   (a) providing a substrate with an organic or inorganic layer formed thereon;
   (b) performing a spectral ellipsometer measurement and a broadband spectrometer measurement of said organic or inorganic layer in an integrated optical measurement system;
   (c) independent of said performing, determining a thickness for said organic or inorganic layer using an independent optical thickness measurement component based on Beam Profile Reflectometry or Beam Profile Ellipsometry;
   (d) determining said values for said optical constants n and k for said organic or inorganic layer based on said thickness, the spectral ellipsometer measurement, the broadband spectrometer measurement, and modeling information, wherein n represents index of refraction and k represents extraction coefficient; and
   (e) displaying an experimental data output for said thickness data of said organic or inorganic layer combined with measurement data from said spectral ellipsometer and broadband spectrometer measurements, wherein said experimental data output is fitted to modeling data to provide a best fit of experimental data to modeling data.

2. The method of claim 1 wherein the integrated optical measurement systems is an Optic-Probe series measurement system from Therma-Wave or a system with equivalent capability.

3. The method of claim 1 wherein the integrated optical measurement systems is an Opti-Probe series measurement system from Therma-Wave or a system with equivalent capability.

4. The method of claim 1 wherein the in the independent optical thickness measurement component provides experimental data in the form of beam profiles that are matched to modeling data in a processor to arrive at a best fit of experimental data to modeling data.

5. The method of claim 1 wherein step (d) involves a Critical Point model otherwise known as a harmonic oscillator approximation.

6. The method of claim 1 wherein said best fit of experimental data to modeling data provides said values for said optical constants n and k for said organic or inorganic layer.

7. The method of claim 1 wherein said organic or inorganic layer is a 248 nm photoresist, a 193 nm photoresist, or an anti-reflective layer.

8. A method for obtaining n and k values for corresponding optical constants n and k for a top layer in a bilayer film stack on a substrate comprising:
   (a) providing a substrate having a stack of layers comprised of a top photoresist layer and a bottom layer formed thereon;
   (b) performing a spectral ellipsometer measurement and a broadband spectrometer measurement of said top photoresist layer in an integrated optical measurement system;
   (c) inputting an input thickness value and input n and k values for said bottom layer into a program used to calculate said n and k values;
   (d) independent of said performing, determining a thickness for said top photoresist layer using an independent optical thickness measurement component based on Beam Profile Reflectometry or Beam Profile Ellipsometry;
   (e) independent of said performing, determining said values n and k values for said top photoresist layer based on data that includes the thickness of said top photoresist layer, the spectral ellipsometer measurement, the broadband spectrometer measurement, and modeling information, wherein n represents index of refraction and k represents extraction coefficient; and
   (f) displaying an experimental data output for said thickness of the top photoresist layer combined with measurement data from said spectral ellipsometer and broadband spectrometer measurements, wherein said experimental data output is fitted to modeling data to provide a best fit of experimental data to modeling data.

9. The method of claim 8 wherein said top photoresist layer has a thickness in the range of about 1000 to 10000 Angstroms.

10. The method of claim 8 wherein the thickness as well as the input n and k values of said bottom layer were determined prior to forming said top photoresist layer by a process comprising:
   (1) forming said bottom layer on said substrate;
   (2) performing a spectral ellipsometer measurement and a broadband spectrometer measurement of said bottom layer in an integrated optical measurement system;
   (3) determining a thickness for said bottom layer; and
   (4) determining said input n and k values for said bottom layer based on the thickness of the bottom layer, spectral ellipsometer measurement of the bottom layer, broadband spectrometer measurement of the bottom layer, and modeling information.

11. The method of claim 10 wherein the independent optical thickness measurement component is used to determine the thickness bottom layer.

12. The method of claim 10 wherein the independent optical thickness measurement component is based on Beam Profile Reflectometry or Beam Profile Ellipsometry.

13. The method of claim 10 wherein the integrated optical measurement system is an Opti-Probe series measurement system for Therma-Wave or a system with equivalent capability.

14. The method of claim 8 wherein step (e) involves a Critical Point model otherwise known as a harmonic oscillator approximation.

15. The method of claim 8 wherein said best fit of experimental data to modeling data provides said values for said optical constants n and k for said top photoresist layer.

16. The method of claim 8 wherein said top photoresist layer is 248 nm photoresist or a 193 nm photoresist and the bottom layer is an organic or inorganic anti-reflective layer.

17. A method for obtaining n and k values for corresponding optical constants n and k for a top layer in a triilayer film stack on a substrate comprising:
   (a) providing a substrate having a stack of layers comprised of a bottom inorganic layer, a middle organic anti-reflective coating layer, and a top photorsist layer formed thereon;
   (b) performing a spectral ellipsometer measurement and a broadband spectrometer measurement of said top photoresist layer in an integrated optical measurement system;
   (c) inputting a thickness and input n and k values for said bottom inorganic layer and said middle anti-reflective coating layer into a program used to calculate said n and k values;
   (d) independent of said performing, determining a thickness for said top photoresist layer using an independent optical thickness measurement component based on Beam Profile Reflectometry or Beam Profile Ellipsometry;
   (e) determining said n and k values for said top photoresist layer based on data that includes the thickness of said top photoresist layer, the spectral ellipsometer measurement, the broadband spectrometer measurement, and modeling information, wherein n represents index of refraction and k represents extraction coefficient; and
   (f) displaying an experimental data output for said thickness of the top photoresist layer combined with measurement data from said spectral ellipsometer and broadband spectrometer measurements, wherein said experimental data output is fitted to modeling data to provide a best fit of experimental data to modeling data.

18. The method of claim 17 wherein said best fit of experimental data to modeling data provides said n and k values for said top photoresist layer.

19. The method of claim 17 wherein said top photoresist layer is a 248 nm or 193 nm photoresist and the bottom inorganic layer is comprised of silicon nitride or silicon oxynitride.

* * * * *

UNITED STATES PATENT AND TRADEMARK OFFICE
CERTIFICATE OF CORRECTION

| | |
|---|---|
| PATENT NO. | : 7,259,850 B2 |
| APPLICATION NO. | : 10/757204 |
| DATED | : August 21, 2007 |
| INVENTOR(S) | : Chih-Ming Ke, Pei-Hung Chen and Shinn-Sheng Yu |

It is certified that error appears in the above-identified patent and that said Letters Patent is hereby corrected as shown below:

Column 10, line 57, delete "in the".

Column 12, line 15, delete "trillayer" and insert therefore -- trilayer --.

Column 12, line 20, delete "photorsist" and insert therefore -- photoresist --.

Signed and Sealed this

Twenty-fifth Day of December, 2007

JON W. DUDAS
*Director of the United States Patent and Trademark Office*